US010967022B2

(12) United States Patent
Rana et al.

(10) Patent No.: US 10,967,022 B2
(45) Date of Patent: *Apr. 6, 2021

(54) BOTANICAL EXTRACT FOR SKIN CARE

(71) Applicant: Innophos, Inc., Cranbury, NJ (US)

(72) Inventors: Jatinder Rana, Grand Rapids, MI (US); Kylie Mitchell, Pennington, NJ (US)

(73) Assignee: Innophos, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/515,097

(22) Filed: Jul. 18, 2019

(65) Prior Publication Data

US 2020/0069754 A1 Mar. 5, 2020

Related U.S. Application Data

(60) Provisional application No. 62/725,441, filed on Aug. 31, 2018.

(51) Int. Cl.
*A61K 36/22* (2006.01)
*A61P 17/18* (2006.01)
*A61P 29/00* (2006.01)
*A61K 8/9789* (2017.01)

(52) U.S. Cl.
CPC ............ *A61K 36/22* (2013.01); *A61K 8/9789* (2017.08); *A61P 17/18* (2018.01); *A61P 29/00* (2018.01)

(58) Field of Classification Search
None
See application file for complete search history.

(56) References Cited

U.S. PATENT DOCUMENTS

| 7,897,184 | B1 | 3/2011 | Rana et al. |
| 8,685,472 | B2 | 4/2014 | Rana et al. |
| 9,333,159 | B2 | 5/2016 | Hayes |
| 10,028,970 | B2 | 7/2018 | Chapal et al. |

FOREIGN PATENT DOCUMENTS

| DE | 202008005904 U1 * | 7/2008 | ............ A23L 25/25 |
| IN | 110037 | 4/1967 | |
| WO | 200404026 A2 | 5/2004 | |
| WO | 2011138608 A2 | 11/2011 | |

OTHER PUBLICATIONS

Iozumi, K. et al., Role of tyronsinase as the determinant of pigmentation in cultured human melanocytes, J. Investigative Dermatology, Jun. 1993, vol. 100, pp. 806-811.
Kubo, I. et al., Tyrosinase inhibitors from Anacardium occidentale fruits, J. Natural Products, Apr. 1994, vol. 57, No. 1, pp. 545-551.
Nesterov, A. et al., 1-(2,4-Dihydroxyphenyl)-3-(2,4-dimethoxy-3-methylphenyl)propane, a novel tyrosinase inhibitor with strong depigmentation effects, Chem. Pharm. Bull., 2008, vol. 56, No. 9, pp. 1292-1296.
Chang, T., An updated review of tyrosinase inhibitors, Int. J. Mol. Sci., 2009, vol. 10, pp. 2440-2475.
Tai, S. et al., Evaluation of depigmenting activity by 8-hydroxydaidzein in mouse B16 melanoma cells and human volunteers, Int. J. Mol. Sci., 2009, vol. 10, pp. 4257-4266.
Alam, N. et al., Consequence of the antioxidant activities and tyrosinase inhibitory effects of various extracts from teh fruiting bodies of Pleurotus ferulae, Saudi J. Biolog. Sci., 2012, vol. 19, pp. 111-118.
Bae-Harboe, Y. et al., Tyrosinase: a central regulatory protein for cutaneous pigmentation, J. Investigative Dermatology, 2012, vol. 132, pp. 2678-2680.
Loizzo, M. et al., Natural and synthetic tyrosinase inhibitors as antibrowning agents: an update, Comprehensive Reviews in Food Science and Food Safety, 2012, vol. 11, pp. 378-398.
Rana, J. et al., Inhibition of melanin content by Punicalagins in the super fruit pomegranate (*Punica granatum*), J. Cosmet. Sci., Nov./Dec. 2013, vol. 64, pp. 445-453.
Uchida, R. et al., Inhibition of tyrosinase activity and melanine pigmentation by 2-hydroxytyrosol, Acta Pharmaceutica Sinica B, 2014, vol. 4(2), pp. 141-145.
Hamad, F. et al., Potential biological applications of bio-based anacardic acids and their derivatives, Int. J. Mol. Sci., 2015, vol. 16, pp. 8569-8590.
Chen, W.-C. et al., Discovery of highly potent tyrosinase inhibitor, T1, with significant anti-melanogenesis ability by zebrafish in vivo assay and computational molecular modeling, Scientific Reports, 2015, vol. 5:7995, pp. 1-8.
Deri, B. et al., The unravelling of the complex pattern of tyrosinase inhibition, Scientific Reports, 2016, vol. 6:34993, pp. 1-10.
Pillaiyar, T. et al., Skin whitening agents: medicinal chemistry perspective of tyrosinase inhibitors, J. Enzyme Inhibition and Medicinal Chemistry, 2017, vol. 32:1, pp. 403-425.
Micillo, R. et al., 2-S-Lipoylcaffeic acid, a natural product-based entry to tyrosinase inhibition via catechol manipulation, Biomimetics, 2017, vol. 2, No. 15, pp. 1-11; doi:10.3390/biomimetics2030015.
Wang, Y. et al., Synergistic promotion on tyrosinase inhibition by antioxidants, Molecules, 2018, vol. 23, No. 106, pp. 1-13; doi:10.3390/molecules23010106.
Kamath, V. et al., Food Chemistry, the efficacy of cashew nut (*Anacardium occidentale* L.) skin extract as a free radical scavenger, 2007, vol. 103, pp. 428-433.
Trox, J. et al., Food Chemistry, Catechin and epicatechin in testa and their association with bioactive compounds in kernels of cashew nut (*Anacardium occidentale* L.), (2011), vol. 128, pp. 1094-1099.
Xu, M. et al., Natural Product Research, 6'-O-Caffeoylarbutin inhibits melanogenesis in zebrafish, 2014, vol. 28, No. 12, pp. 932-934.
Chandrasekara, Neel et al., Effect of roasting on phenolic content and antioxidant activities of whole cashew nuts, kernals, and testa, J. Agric. Food Chem., 2011, vol. 59, pp. 5006-5014.

(Continued)

*Primary Examiner* — Susan Hoffman
(74) *Attorney, Agent, or Firm* — David LeCroy

(57) ABSTRACT

A botanical extract for use in skin care, wherein the botanical extract is at least an extract from the testa of the seed of *Anacardium occidentale* L.

8 Claims, 3 Drawing Sheets

(56) References Cited

OTHER PUBLICATIONS

Mathew, A.G. et al., Polyphenols of cashew kernal testa, J. Food Science, 1970, vol. 35, pp. 140-143.
Sato, Kazuomi et al., Depigmenting effect of catechins, Molecules, vol. 14, No. 11, Nov. 4, 2009, pp. 4425-4432.
Tang, Haifeng et al., Understanding the inhibitory mechanism of tea polyphenols against tyrosinase using fluorescence spectroscopy, cyclic voltammetry, oximetry, and molecular simulations, RSC Adv., 2018, vol. 8, pp. 8310-8318.
PCT/US2019/041621 PCT International Search Report, dated Oct. 17, 2019.
PCT/US2019/041621 PCT Written Opinion, dated Oct. 17, 2019.

\* cited by examiner

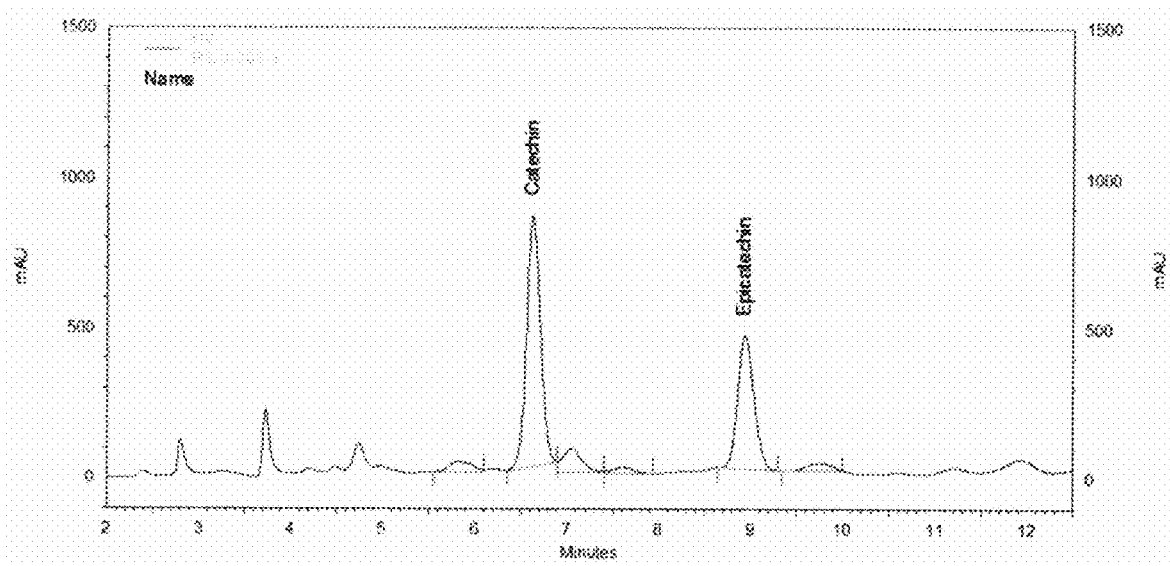
Figure 1 – HPLC Chromatogram of Cashew Testa Extract at 275 nm wavelength

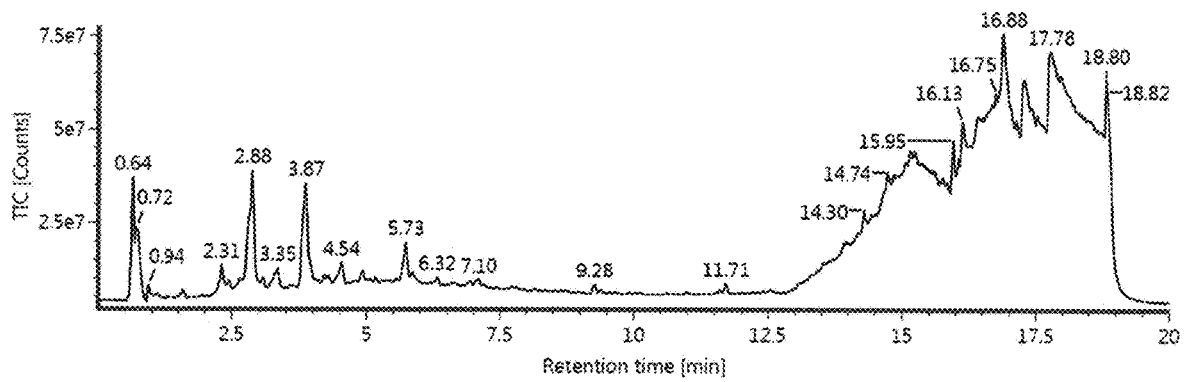
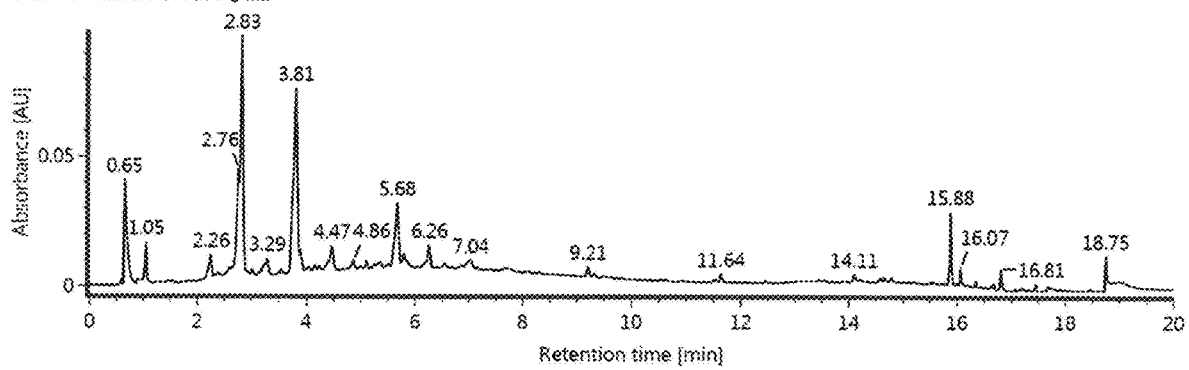
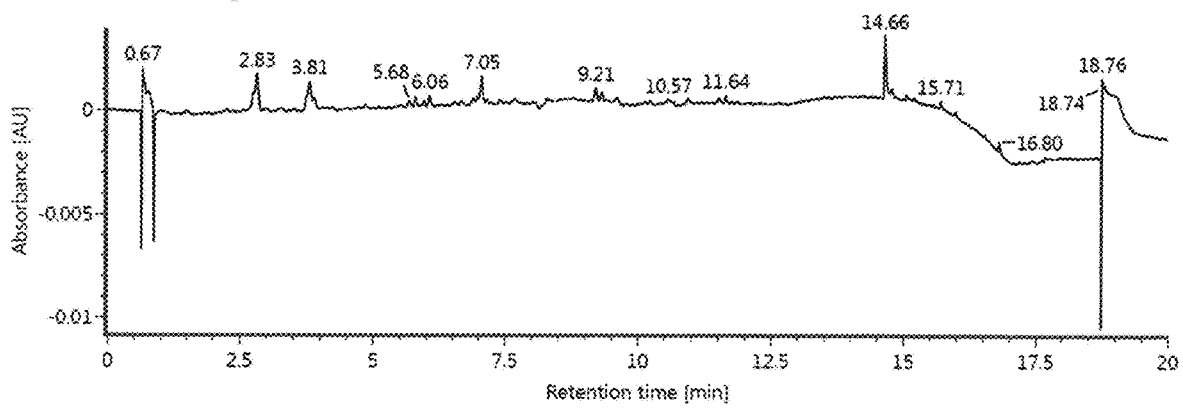
Figure 2 – LC/MS and LC/PDA (280/350 nm) Chromatograms of Cashew Testa Extract

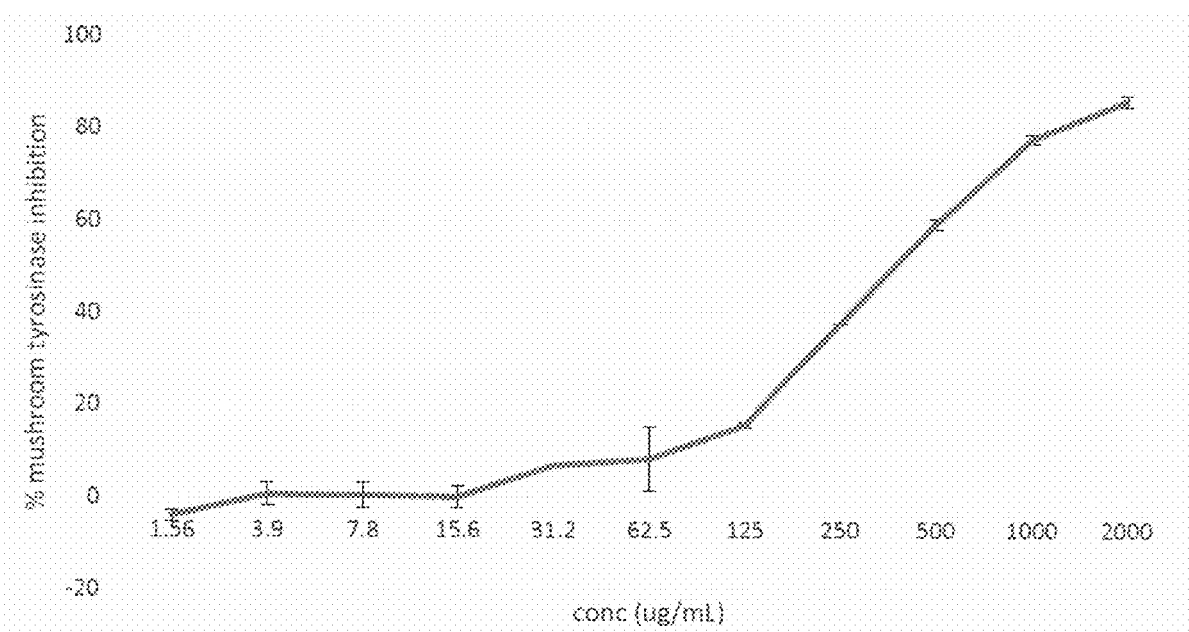
Figure 3 – Cashew Testa Extract Mushroom Tyrosinase Inhibition at 10 Different Concentrations

BOTANICAL EXTRACT FOR SKIN CARE

CROSS REFERENCE TO RELATED APPLICATIONS

The present application claims the benefit of U.S. Patent Application No. 62/725,441, filed 31 Aug. 2018, the disclosure of which is incorporated herein in its entirety by reference.

BACKGROUND OF THE INVENTION

Field of the Invention

The present invention generally relates to botanical extracts for use in skin care applications, including inhibitors of tyrosinase, and more particularly to botanical extracts from cashew testa and the use of such plant-based inhibitors as a skin protectant and/or for skin lightening.

It is believed that approximately 15 percent of the world population invest in skin whitening agents. Analysts have predicted that the universal market for skin lighteners will reach $23 billion by 2020. The molecular mechanism of these skin lightening agents are to reduce the melanin, which is the main source of skin color.

Tyrosinase is a copper-containing enzyme, widely distributed in fungi, plant, and animal tissues. Tyrosinase is a critical enzyme in the production of melanin in melanocytes. Tyrosinase inhibition is one way to prevent melanin production, among others, and many skin whitening products on the market specifically target it.

Synthetic tyrosinase inhibitors, such as hydroquinone, kojic acid, and arbutin, have been reported to cause skin irritation or acute dermatitis, raising concerns about the safety of these compounds. As a consequence, many pharmacologic agents have been studied for their potential to inhibit tyrosinase, with phytomedicine playing an important role. Studies have shown that the consumption of polyphenolic compounds found in various herbs, fruits, and vegetables is associated with inhibition of melanin content. Consequently, there is a growing research interest in plants that exhibit tyrosinase inhibitory activity and health-promoting phytoconstituents as potential therapeutic agents. Medicinal plants can provide a safe, cost-effective, ecological alternative to chemical inhibitors, which, as noted above, can have adverse effects.

The cashew tree (*Anacardium occidentale* Linn) is originally from the Amazon, and has subsequently been transplanted to India, Eastern Africa, and other countries for cultivation. The tree produces a very peculiar apple or fruit in the form of a swollen peduncle. Externally at the end of this peduncle the cashew nut (or seed) grows in its own grey colored kidney-shaped hard shell. This shell has a soft leathery outer skin and a thin hard inner skin referred to as the husk or testa, which surrounds the kernel. Between these two skins is a honeycomb structure containing the cashew nut shell liquid. This liquid comprises anacardic acid, cardanol, and cardol, among other ingredients. Anacardic acid is a salicylic acid, while cardanol and cardol are substituted phenols.

The various parts of the fruit have been studied for their uses. In addition to being an edible food, the juice from the cashew apple is used in beverages, while the fruit extract has shown benefit in weight management. Cashew nut shell liquid has been extracted for various industrial and agricultural applications, including friction linings, paints, laminating resins, rubber, compounding resins, cashew cements, polyurethane based polymers, surfactants, epoxy resins, foundry chemicals, chemical intermediates, insecticides, and fungicides. Cashew testa has been used in tanning materials.

As noted above, there is a need for effective, nontoxic, natural compounds with tyrosinase inhibitory activity. Further, there is a need for effective, nontoxic, natural compounds for use in skin care compositions. The present invention provides one such solution.

BRIEF SUMMARY OF THE INVENTION

Disclosed herein is a botanical extract comprising catechins, wherein the extract has been standardized to a catechin content of about 15.0 w/w % or greater, based on total weight of the extract, wherein the botanical extract exhibits tyrosinase inhibition activity, and wherein the botanical extract comprises at least an extract from the genus *Anacardium*. In particular, the botanical extract is at least an extract from *Anacardium occidentale* L, more particularly from at least the testa of the seed of *Anacardium occidentale* L.

In one embodiment, the botanical extract from at least the testa of the seed of *Anacardium occidentale* L. exhibits antioxidant activity by increased expression of the gene MT1A.

In a further embodiment, the botanical extract from at least the testa of the seed of *Anacardium occidentale* L. exhibits antioxidant activity by increased expression of the gene NQO1.

In another embodiment, the botanical extract from at least the testa of the seed of *Anacardium occidentale* L. exhibits antioxidant activity by increased expression of the gene TXNRD1.

In even another embodiment, the botanical extract from at least the testa of the seed of *Anacardium occidentale* L. exhibits wound healing activity by suppression of the expression of the gene CTGF.

In a further embodiment, the botanical extract from at least the testa of the seed of *Anacardium occidentale* L. exhibits anti-inflammatory activity by increased expression of the genes IL1α and IL1β.

The present invention further provides for a composition comprising the botanical extract of the testa of the seed of *Anacardium occidentale* L., wherein the botanical extract exhibits tyrosinase inhibition activity. Preferably, the botanical extract is present in an amount of about 1.0 μg/mL or greater. More preferably, the botanical extract is present in an amount of about 1.0 μg/mL to about 2000.0 μg/mL. In one embodiment, the composition is a cosmetic composition.

Also provided herein is a dietary supplement having tyrosinase inhibition properties, wherein the supplement comprises a cashew testa extract in a therapeutically effective amount. Preferably, the cashew testa extract is present in an amount of about 1.0 μg/mL or greater.

Further provided herein is a method of inhibiting melanin production in a subject by administering a composition comprising the botanical extract of the testa of the seed of *Anacardium occidentale* L. at a concentration of about 1.0 μg/mL to about 2000.0 μg/mL.

BRIEF DESCRIPTION OF THE SEVERAL VIEWS OF THE DRAWINGS

FIG. 1 is an HPLC chromatogram of cashew testa extract at 275 nm wavelength over a retention time of from 0 minutes (start) to 20 minutes.

FIG. 2 is LC/MS and LC/PDA (wavelengths of 280 and 350 nm) chromatograms of cashew testa extract.

FIG. 3 is a graph illustrating percentage Mushroom Tyrosinase inhibition using cashew testa extract at various (10 different) concentrations.

DETAILED DESCRIPTION OF THE INVENTION

The present invention is based on the surprising discovery that the testa of the cashew (*Anacardium occidentale* Linn) is substantially high in certain flavonoids. In particularly, it has been discovered that the extract of cashew testa comprises catechin and epicatechin as major components, as well as procyanidins. Data noted herein demonstrates that cashew testa extract may have tyrosinase inhibition applications.

For the present application, the term "composition" refers to a product that treats, improves, promotes, increases, manages, controls, maintains, optimizes, modifies, reduces, inhibits, or prevents a particular condition associated with a natural state, biological process or disease or disorder. For example, a composition improves the inhibition of tyrosinase and/or enhances skin whitening, and the like in a subject. The term composition includes, but is not limited to, pharmaceutical (i.e., drug), over-the counter (OTC), cosmetic, food, food ingredient or dietary supplement compositions that include an effective amount of an extract, at least one component thereof, or a mixture thereof. Exemplary compositions include cream, cosmetic lotion, pack or powder, or as an emulsion, lotion, liniment foam, tablets, plasters, granules, or ointment. Such compositions include topical compositions in the form of a liquid, lotion, cream or powder. Compositions can also include beverages, for example, beverages infused with an effective amount of an extract, or a tea satchel containing an effective amount of an extract. Non-limiting examples of food compositions containing an effective amount of an extract include baked goods, protein powders, meat products, dairy products, and confectionary.

The terms "skin whitening", "whitening skin", or "skin lightening" refer to one or more effects of suppressing melanin production or melanin content in an individual, including prevention or inhibition of pigmentation, lightening of dark skin, lightening or removal of hyperpigmentations, especially local hyperpigmentations and defective pigmentations; prevention and/or improvement of skin dullness, skin darkening by sunburn, spots, and freckles.

As used herein, the term "extract" or "botanical extract" refers to a solid, viscid, or liquid substance or preparation that includes one or more active ingredients of a substance of at least the plant *Anacardium* (e.g., *Anacardium humile, Anacardium othonianum, Anacardium giganteum, Anacardium nanum, Anacardium negrense,* and/or *Anacardium occidentale*), preferably *Anacardium occidentale* L. Preferably, the active ingredient is derived from the extract of the testa of the cashew. The extract is prepared using a solvent such as water, lower alcohols of 1 to 4 carbon atoms (e.g., methanol, ethanol, butanol, etc.), ethylene, acetone, hexane, ether, chloroform, ethylacetate, butylacetate, dichloromethane, N,N-dimethylformamide ('DMF'), dimethylsulfoxide ('DMSO'), 1,3-butylene glycol, propylene glycol, and combinations thereof, but also a fraction of the crude extract in such a solvent. So long as it assures the extraction and preservation of the active ingredient(s), any extraction method may be employed.

As used herein, the term "effective amount" or "therapeutically effective amount" of a pure compound, composition, extract, extract mixture, component of the extract, and/or active agent or ingredient, or a combination thereof refers to an amount effective at dosages and for periods of time sufficient to achieve a desired result. For example, the "effective amount" or "therapeutically effective amount" refers to that amount of a pure compound, composition, extract, botanical extract, extract mixture, botanical extract mixture, component of the extract, and/or active agent or ingredient, or a combination thereof of this invention which, when administered to a subject (e.g., mammal, such as a human), is sufficient to effect treatment, such as improving the inhibition of oxidation and/or reducing inflammation, and the like in a subject. The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "administer", "administered", "administers", and "administering" are defined as providing a composition to a subject via a route known in the art, including but not limited to intravenous, intra-arterial, oral, parenteral, buccal, topical, transdermal, rectal, intramuscular, subcutaneous, intraosseous, transmucosal, or intraperitoneal routes of administration. In preferred embodiments, oral routes of administering a composition are suitable.

As used herein, the term "subject" or "individual" includes mammals to which a composition may be administered. Non-limiting examples of mammals include humans, non-human primates, canines, felines, equines, bovines, rodents (including transgenic and non-transgenic mice) or the like. In some embodiments, the subject is a non-human mammal, and in some embodiments, the subject is human.

As used herein, the term "carrier" refers to a composition that aids in maintaining one or more plant extracts in a soluble and homogeneous state in a form suitable for administration, which is nontoxic and which does not interact with other components in a deleterious manner.

Unless indicated otherwise, all proportions and percentages recited throughout this disclosure are by weight.

The present invention provides a plant-based inhibitor capable of tyrosinase inhibition. More particularly, the present invention is directed towards a botanical extract of the cashew testa from the genus *Anacarium*. Such botanical extracts have been found to be capable of inhibiting tyrosinase.

Useful botanical extracts capable of tyrosinase inhibition according to the present invention include botanical extracts from the genus *Anacardium*. More particularly, the plant-based inhibitor is a botanical extract chosen from one or more of the species *Anacardium humile, Anacardium othonianum, Anacardium giganteum, Anacardium nanum, Anacardium negrense,* and/or *Anacardium occidentale.* Preferably, the botanical extract is from the species *Anacardium occidentale*. In one embodiment, the botanical extract is from the testa of the species *Anacardium occidentale*.

Compositions capable of tyrosinase inhibition according to the present invention may include one or more compounds that may function as active ingredients. The compound may be a component of the botanical extract. For example, the compound can be a phytochemical present in the plant from which the plant extract is obtained. The compound may be at least partially responsible for tyrosinase inhibition. The compound can be any compound capable of tyrosinase inhibition. In one embodiment, the compound is chosen from the phytochemicals catechins, epicatechins, and/or procyanidins (e.g., A, B, trimer, tetramer).

Generally, one or more parts of a plant can be used to produce a plant extract including, but not limited to, the root, the stem, the leaf, the flower, the fruit, the seed, and the testa of the seed. In the present invention, at least the testa of the seed is used—alone or with other plant parts—to produce the plant extract. The testa from the *Anacardium* plant can be commercially obtained from various sources. The extract of the cashew testa can be obtained using any suitable extraction technique.

In this regard, one or more parts of the plant, particularly the testa of the plant, can be collected and milled. Thereafter, the milled material can be extracted using a suitable solvent. The solvent can be removed in a concentration step. For example, the extracted material can be screened or filtered to create a supernatant and a cake. The cake can be pressed to remove a substantial portion of the liquid, which can be added to the supernatant. The cake can then be dehydrated and used as a fiber source. The supernatant can be distilled to remove the solvent or a portion thereof, to form a plant extract liquid concentrate. The removed solvent can be recycled. The concentrate can be dried (e.g., by spray drying) to provide a dried plant extract. This dried plant extract can be assayed and/or standardized as described herein. Preferably, the dried plant extract is derived from *Anacardium occidentale*, particularly the testa of the plant *Anacardium occidentale*.

Suitable solvents for the extraction process include water, alcohol, or mixtures thereof. Exemplary alcoholic solvents include, but are not limited to, $C_1$-$C_7$ alcohols (e.g., methanol, ethanol, propanol, isopropanol, and butanol), hydroalcohols or mixtures of alcohol and water (e.g., hydroethanol), polyhydric alcohols (e.g., propylene glycol and butylene glycol), and fatty alcohols. Any of these alcoholic solvents can be used in the form of a mixture. In one embodiment, the plant extract is extracted using ethanol, water, or a combination thereof (e.g., a mixture of about 70% ethanol and about 30% water). In another embodiment, the plant extract is extracted using only water.

In one embodiment, the plant extract can be obtained using an organic solvent extraction technique. In another embodiment, solvent sequential fractionation can be used to obtain the plant extract. Total hydro-ethanolic extraction techniques can also be used to obtain the plant extract. Generally, this is referred to as a lump-sum extraction.

Total ethanol extraction can also be used. This technique uses ethanol as the solvent. This extraction technique can generate a plant extract having fat soluble and/or lipophilic compounds in addition to water soluble compounds.

Another example of an extraction technique that can be used to obtain the plant extract is supercritical fluid carbon dioxide extraction ('SFE'). In this extraction procedure, the material to be extracted may not be exposed to any organic solvents. Rather, carbon dioxide can be used as the extraction solvent—with or without a modifier—in super-critical conditions (>31.3° C. and >73.8 bar). Those skilled in the art will appreciate that temperature and pressure conditions can be varied to obtain the best yield of extract. This technique can generate an extract of fat soluble and/or lipophilic compounds, similar to a total hexane and ethyl acetate extraction technique.

The plant extract generated in the process can include a broad variety of phytochemicals present in the extracted material. The phytochemicals can be fat soluble or water soluble. Following collection of the extract solution, the solvent can be evaporated, resulting in the extract.

The plant extract can be standardized to a specified amount of a particular compound. For example, the plant extract can be standardized to a specified amount of an active ingredient or phytochemical present in the extract. In one embodiment, the plant extract is standardized to a catechin content of about 15.0 wt % or greater, based on total weight of the extract.

The amount of plant extract present in the tyrosinase inhibition composition can depend upon several factors, including the desired level of tyrosinase inhibition, the tyrosinase inhibition level of a particular plant extract or component thereof, and other factors. Preferably, the plant extract is present in an amount of from about 0.005 wt % or greater, for example, from about 0.005 wt % to about 50.00 wt %, based on total weight of the composition.

The tyrosinase inhibition composition can include one or more acceptable carriers. The carrier can aid in enabling incorporation of the plant extract into a tyrosinase inhibiting composition having a suitable form for administration to a subject. A wide number of acceptable carriers are known in the art, and the carrier can be any suitable carrier. The carrier is preferable suitable for administration to animals, including humans, and can be able to act as a carrier without substantially affecting the desired activity of the plant extract and/or any active ingredient. The carrier can be chosen based upon the desired administration route and dosage form of the composition.

Suitable dosage forms include liquid and solid forms. In one embodiment, the composition is in the form of a gel, a syrup, a slurry, or a suspension. In another embodiment, the composition is in a liquid dosage form such as a drink shot or a liquid concentrate. In a further embodiment, the composition is present in a solid dosage form, such as a tablet, a pill, a capsule, a dragée, or a powder. When in liquid or solid dosage form, the composition can be in a food delivery form suitable for incorporation into food for delivery. Examples of suitable carriers for use in solid forms (particularly tablet and capsule forms) include, but are not limited to, organic and inorganic inert carrier materials such as gelatin, starch, magnesium stearate, talc, gums, silicon dioxide, stearic acid, cellulose, and the like. The carrier can be substantially inert.

As an example, silicified microcrystalline cellulose can be used as a carrier or binder. Silicified microcrystalline cellulose is a physical mixture of microcrystalline cellulose and colloidal silicon dioxide. One such suitable form of silicified microcrystalline cellulose is ProSolv SMCC® 90, available from Penwest Pharmaceutical Co., Patterson, N.J. Silicon dioxide, in addition to that provided by the silicified microcrystalline cellulose, may be added to the composition as a processing aid. For example, silicon dioxide can be included as a glidant to improve the flow of powder during compression in the manufacturing of solid dosage units, such as tablet.

In another embodiment, the carrier is at least a functional carrier such as buckwheat or spelt. By the addition of functional carriers into the composition, additional benefits may be provided such as lower glycemic index compared to standard carriers such as those mentioned above. Further, functional carriers can be allergan free (e.g., buckwheat), and by adding them into the production process, the botanical extracts of the invention may benefit from the flavonoids of these functional carriers, such as rutin and quercetin. Further, the high fiber content of these functional carriers may also facilitate and regulate intestinal transit. Finally, the added mineral benefit of selenium found in spelt may aid in metabolism.

The tyrosinase inhibition composition can include other inert ingredients, such as lubricants and/or glidants. Lubricants aid in the handling of tablets during manufacturing, such as during ejection from dies. Glidants improve powder flow during tablet compression. Stearic acid is an example of an acceptable lubricant/glidant.

The tyrosinase inhibition composition can be made in solid dosage form, such as tablets and capsules. This form provides a product that can be easily transported by an individual to a place of eating, such as a restaurant, and taken prior to, during, or after consumption of a foodstuff. The composition can be formulated into dosage units containing suitable amounts of the plant extract and/or active ingredient that permit an individual to determine an appropriate number of units to take based upon appropriate parameters, such as body weight, foodstuff size, or carbohydrate (e.g., sugar) content.

In one embodiment, the botanical extract is present in the composition in a therapeutically effective amount, such as an amount of about 4 μg/mL or greater, preferably from about 4.0 μg/mL to about 2000.0 μg/mL, more preferably from about 15.0 μg/mL to about 1000.0 μg/mL, even more preferably from about 30.0 μg/mL to about 500.0 μg/mL. The composition can be administered as a single dose, or in multiple doses. In one example, the compound is administered in up to three doses per day. For example, the compound may be administered prior to a meal, during a meal, or after a meal. In one embodiment, the composition is a dietary supplement having tyrosinase inhibition properties containing cashew testa extract in a therapeutically effective amount.

The dosage can be chosen to provide a level of inhibitory effect in a single unit that may be effective for some individuals and/or some foodstuffs, while also allowing for relatively simple dosage increases to provide other levels of inhibitory effects that can be effective for other individuals and/or other foodstuffs.

The inhibiting composition can be in a form adapted for oral ingestion. This form can be configured as a single dosage form intended to provide a specified dose of the plant extract. For example, the single dosage form can be a powder, a pill, a tablet, a capsule, or a drink shot. The single dosage form can include, for example, from about 4.0 μg/mL to about 2000.0 μg/mL of the plant extract.

EXAMPLES

Examples—Materials and Chemical Profiling

Example 1—Preparation of Cashew Testa Extract Using 70% Ethanol Solvent

Dried cashew testa powder (*Anacardium occidentale*) (60 g) was loaded into three 100 ml stainless steel tubes and extracted twice using a solvent of 70% ethanol in DI water with a Thermo Scientific™ Dionex™ ASE 350 Accelerated Solvent Extractor at a temperature of 80° C. and pressure of 1500 psi. The extract solution was filtered and collected. The combined ethanol extract solution was evaporated with a rotary evaporator under vacuum to give a crude cashew testa extract.

The extraction results are provided in the following Table 1—

TABLE 1

| Extraction of cashew testa | | | |
|---|---|---|---|
| Plant Part | Plant Powder (g) | Extract Weight (g) | Extraction Yield (wt %) |
| Testa | 60 | 23.78 | 39.63% |

Example 2—Catechin Quantification of Cashew Testa Extract

Free catechins present in the cashew testa extract were determined using a C18 reversed-phase column (Luna® 5 μm C18(2) 100 Å LC Column 250×4.6 mm, available from Phenomenex®, Torrance, Calif., US) together with an Hitachi high performance liquid chromatograph with photodiode array detector ('HPLC/PDA'). For mobile phase A, the solvent was 0.10% phosphoric acid ('$H_3PO_4$') in water, and for mobile phase B, the solvent B was acetonitrile ('ACN'), which was used for elution at a flow rated of 1.0 ml/min with UV absorbance at 275 nm and a column temperature of 35° C. Catechin reference standards used were from Sigma-Aldrich Co. The reference standards were dissolved in methanol ('MeOH') 0.1% $H_3PO_4$ (1:1 ratio) with catechin (C1251) at a concentration of 0.5 mg/ml and epicatechin (E1753) at 0.1 mg/ml. Testing samples were prepared at 2 mg/ml in 50% MeOH in 0.1% $H_3PO_4$ in a volumetric flask and sonicated until dissolved (approximately 10 minutes), and then cooled to room temperature, mixed well, and filtered through a 0.45 μm nylon syringe filter. HPLC analysis was performed by injecting a 20 μl sample into the HPLC. Table 2 below provides the gradient table of HPLC analytical method—

TABLE 2

| Gradient Table of HPLC Analytical Method | | |
|---|---|---|
| Time (min) | Mobile Phase A | Mobile Phase B |
| 0.0 | 85.0 | 15.0 |
| 7.0 | 85.0 | 15.0 |
| 12.0 | 10.0 | 90.0 |
| 16.5 | 10.0 | 90.0 |
| 16.6 | 85.0 | 15.0 |
| 24.0 | 85.0 | 15.0 |

HPLC Catechin quantification results in cashew testa extract provided a catechin content of 9.40% and an epicatechin content of 6.12%, for a total catechin content of 15.52% by weight, based on total weight of the extract. Accordingly, the cashew testa extract can be standardized to a total catechin content of about 15.00% or greater by weight, based on total weight of the extract. The HPLC chromatogram for cashew testa extract at 275 nm wavelength is provided in FIG. 1.

Example 3—Chemistry Profiling of Cashew Testa Extract

Flavonoid compounds present in the cashew testa extract were determined using ultra high pressure liquid chromatography ('HPLC') and mass spectrometry (ACQUITY® UPLC I-Class and XEVO® GS-XT-QTof system, both available from Water Corporation, Milford, Mass. USA). The column used was an ACQUITY® UPLC HSS T3 2.1×100 mm, 1.8 µm, with a column temperature of 40° C. and a sample temperature of 15° C. For the mobile phase, Solvent A was 10% acetonitrile ('ACN') in water (0.1% Formic Acid), and Solvent B was ACN. The acquisition range was 100-1500 Daltons ('Da'), and the acquisition mode was electrospray ionization ('ESI') (−). Table 3 below provides the HPLC conditions—

TABLE 3

HPLC conditions for analyzing cashew testa extract

| Run Time (min) | Injection Volume (µL) | Concentration |
|---|---|---|
| 20.00 | 2.00 | 1 mg/mL |

Peak identification was based on accurate mass only. Digalloyl catechin, catechin and epicatechin were identified as the major components for cashew testa extract. Procyanidins were detected in the extract as well, including A- and B-type procyanidins, procyanidin tetramer, and procyanidim trimer, with B-type procyanidins being the major component of the procyanidins. Compounds identified, in addition to those just mentioned, included digalloyl catechin, vaccihein A, 6"-p-coumaroylprunin, and dunalianoside B, among others. LC/MS and LC/PDA chromatograms of cashew testa extract obtained from the analysis are illustrated in FIG. 2.

Examples—Bioassay

Extracts of cashew testa were prepared with food-grade ethanol, and then filtered and dried as described above. Research grade reagents were used for the rest of the assay preparations. Extracts were dissolved in dimethyl sulfoxide ('DMSO') to a final concentration of 50 mg/mL, and then diluted in appropriate buffer for each bioassay to working concentrations.

Example 4—Mushroom Tyrosinase Inhibition

Cashew testa extract was analyzed for its inhibitory effect on the mushroom tyrosinase enzyme. Cashew testa extract was diluted in Assay Buffer (100 mM sodium phosphate, pH 6.8) with 10% dimethyl sulfoxide ('DMSO') to test concentrations. L-DOPA amino acid substrate solution was prepared in fresh Assay Buffer. Samples and L-DOPA (final 1 mM concentration) were mixed in a microplate before the addition of 10 units of mushroom tyrosinase enzyme. Absorbance at 492 nm was read at 5 and 10 minutes with calculations performed on the 5 minute data. Percent inhibition was calculated relative to the untreated controls.

Mushroom tyrosinase activity was measured by mixing mushroom tyrosinase with a substrate—L-DOPA—in the presence of potential inhibitors and measuring the presence of reaction products at 492 nm. Percentage mushroom tyrosinase inhibition for cashew testa extract is provided in FIG. 3. From FIG. 3, it is seen that cashew testa extract has an inhibitory effect on the mushroom tyrosinase enzyme. As illustrated, at least 50% mushroom tyrosinase inhibition occurs at a cashew testa extract concentration of from about 15.0 µg/mL or greater. More specifically, at least 50% mushroom tyrosinase inhibition occurs at a concentration of about 15.0 µg/mL or greater; preferably from about 15.0 µg/mL to about 2000.0 µg/mL; more preferably from about 125.0 µg/mL to about 1000.0 µg/mL. In particular, cashew testa extract exhibits an $IC_{50}$ of about 391 µg/mL.

Example 5—Gene Expression

Cashew testa extract was explored to determine how it influences gene expression in the skin when added to a culture medium. The study was performed using a full-thickness in vitro skin culture model containing epidermal and dermal cell layers (EpiDermFT™ (full thickness) tissue model, from MatTek Corporation, Ashland, Mass., US). Gene expression was assessed in full-thickness tissues following 24-hour exposure.

A control ('Vehicle Control') was prepared as a blend of dimethyl sulfoxide ('DMSO'), ethanol, and water in a 70:20:10 ratio. Cashew testa extract in three different concentrations—500 µg/mL, 1000 µg/mL, and 2000 µg/mL—were applied to the cell culture medium to determine cell viability. An equivalent volume of the Vehicle Control was also applied for each at 0.5%, 1.0% and 2.0%, respectively. One culture was treated for 24 hours with 1% Triton X-100 to serve as a negative (−) MTT control. Untreated cultures served as the positive (+) control. Following a 24-hour incubation, an MTT assay was performed.

Cell viability was <80% in the 2000 µg/mL concentration of cashew testa extract (74%), but was >100% for the 500 µg/mL (126%) and 1000 µg/mL (105%) concentrations. The 500 µg/mL concentration was selected for gene expression analysis.

Treatment and Maintenance of Cultures—EFT-400 tissues (MatTek Corporation) were equilibrated overnight at 37° C. with 5% $CO_2$ and approximately 95% relative humidity. The following day equilibration medium was removed and replaced with cashew testa extract medium. A 2.5 mL volume of medium was added to each EFT-400 culture well.

MTT portion—Three replicate cultures were included for each group. For the MTT(+) tissues, three tissues were cultured with untreated EFT-400-ASY medium. For the MTT(−) tissues, a 100 µL volume of 1% Triton X-100 was applied to the surface of each EFT culture and incubated with untreated EFT-400-ASY medium. Following the addition of the cashew testa extract medium, cultures were returned to the incubator at 37° C. with 5% $CO_2$ and approximately 95% relative humidity for 24 hours.

Gene expression portion—Four replicates were included for each group. Following the addition of the cashew testa extract medium, cultures were returned to the incubator at 37° C. with 5% $CO_2$ and approximately 95% relative humidity for 24 hours. After 24 hours, the extract medium from each well was collected for an LDH assay (described below). Then each EFT-400 culture was cut into quarters and placed into a tube containing RNAlater preservative solution for a 2-hour incubation at room temperature, then moved to 4° C. Following a four-day incubation in RNAlater preservative solution at 4° C., RNA was isolated from each tissue as described below.

MTT Viability Assay—Each culture was incubated for 3 hours±5 minutes with 1 mg/mL MTT thiazolyl blue tetrazolium bromide powder (M5655 from Sigma-Aldrich). After 3 hours, the MTT medium was removed. Tissues were then blotted on a sterile kimwipe to remove any excess MTT medium and then placed in an extraction well. Tissues were submersed in 100% isopropyl alcohol and incubated at ambient temperature on a plate shaker for 2 hours to solubilize the formazan salts. Following the 2-hour incubation, the tissues were removed from each extraction well, leaving behind only the solubilized formazan salts in isopropanol.

200 µL aliquots of extract from each well were transferred into duplicate wells of a 96-well microtiter plate. Absorbance at 570 nm was measured using a Multiskan™ FC Microplate Photometer (from Thermo Scientific™). Fresh isopropyl was measured as a blank, with the mean absorbance of the blank subtracted from the other sample readings. Culture viability for each culture was calculated by comparing the mean A570 reading of each test group to the mean A570 reading of the untreated control group using the following formula:

% Viability=[Treated $A_{570}$/Untreated $A_{570}$]*100

LDH Cytotoxicity Assay—The collected EFT culture medium (cashew testa extract test medium) was diluted 1:10 with sterile phosphate-buffered saline ('PBS'). The LDH reaction mixture (from TaKaRa Bio Inc.) was prepared and added to an aliquot of diluted medium in an optically clear, flat-bottom 96-well plate (1:1). A background control (diluted EFT medium that was not used for cell culture), a "Low Control" (diluted EFT medium collected from untreated EFT culture wells), and a "High Control" (diluted EFT medium collected from 1% Triton X-100 treated culture wells) were included in the assay. Each sample was assayed with duplicate reaction wells.

The reaction wells were incubated for approximately 25 minutes at room temperature, and protected from light. A stopping solution (0.1N HCl) was then added to each well and absorbance was measured at 492 nm with a reference filter at 620 nm. Each sample absorbance value was calculated as the mean OD492-OD620 value for the duplicate reaction wells, with the blank absorbance value subtracted. The % Cytotoxicity was then calculated relative to the untreated (negative control, set to 0% cytotoxicity) and the Triton X-100 treated (positive control, set to 100% cytotoxicity) absorbance values as follows:

% Cytotoxicity=[(Test Media Value−Low Control)/ (High Control−Low Control)]*100

RNA Isolation—RNA was isolated from each tissue using a Maxwell® 16 LEV simply RNA Purification Kit (available from Promega Corporation) following manufacturer's instructions. The RNA samples were all above 200 ng/µL at isolation—the concentration required for OpenArray processing—and did not need vacuum concentration. RNA concentration and purity were determined using a NanoDrop 2000 Spectrophotometer.

cDNA Synthesis—cDNA was generated using a High-Capacity cDNA Reverse Transcription Kit (available from Applied Biosystems™) according to the manufacturer's instructions. For OpenArray processing of 112 Standard Skin Panel genes, cDNA was generated from 2000 ng RNA per sample.

qPCR Processing—qPCR reactions were run using validated TaqMan Gene Expression Assays (from Applied Biosystems™). OpenArrays were run in a Life Technologies QuantStudio 12K Flex instrument. Each gene was assayed in duplicate.

Data Analysis—qPCR data quality was assessed and exported from the raw data files using Expression Suite software (Life Technologies). qPCR data was then imported into the "OmicsOffice for qPCR" tool of TIBCO Spotfire Analyst software. Statistical analysis was performed using the relative quantitation (RQ) method. In the first step of an RQ analysis, the CT value of the target gene is normalized to the CT value of an endogenous control gene to generate the delta CT (dCT). dCT values are calculated in order to normalize for variability between the samples that may occur during the experimental procedures.

Statistical Data Analysis Using TIBCO Spotfire Software—Unpaired t-tests were carried out using TIBCO Spotfire software, with and without an optional Benjamini-Hochberg false discovery rate (FDR) p-value adjustment applied. Statistically significant (unpaired t-test, FDR p≤0.05, N=4) changes in gene expression are reported in Table 4 below—

TABLE 4

Statistically Significant Changes in Gene Expression Versus Vehicle Control

| Gene | 500 µg/mL Cashew Testa Extract | | Biological function in skin |
|---|---|---|---|
| | % change | Linear FC | |
| AHR | n.s. | n.s. | Antioxidant/stress response |
| GPX1 | n.s. | n.s. | |
| HMOX1 | n.s. (+23%) | n.s. (1.23) | |
| MT1A | +156% | 2.56 | |
| NFE2L2 | n.s. | n.s. | |
| NQO1 | +160% | 2.60 | |
| SOD1 | n.s. | n.s. | |
| TXN | n.s. (+22%) | n.s. (1.22) | |
| TXNRD1 | +104% | 2.04 | |
| CASP14 | +53% | 1.53 | Cell renewal/regeneration |
| CASP3 | n.s. (+28%) | n.s. (1.28) | |
| GSK3B | n.s. | n.s. | |
| PCNA | n.s. | n.s. | |
| PPARG | n.s. | n.s. | |
| CTGF | −75% | −4.06 | Growth factor/wound healing |
| EGFR | n.s. | n.s. | |
| HBEGF | n.s. | n.s. | |
| ICAM1 | +159% | 2.59 | |
| VEGFA | n.s. | n.s. | |
| ADAM17 | n.s. (+32%) | n.s. (1.32) | Inflammation/immune response |
| DEFB1 | −20% | −1.25. | |
| IFNA1 | n.s. | n.s. | |
| IL1A | +63% | 1.63 | |
| IL1B | +615% | 7.15 | |
| IL23A | n.s. | n.s. | |
| MAP3K7 | n.s. (+20%) | n.s. (1.20) | |
| PTGS1 | n.s. (−22%) | n.s. (−1.28) | |
| BIRC5 | −52% | −2.09 | Anti-aging |
| HNRNPD | n.s. | n.s. | |
| SIRT1 | n.s. | n.s. | |
| MMP1 | +291% | 3.91 | Extracellular matrix breakdown |
| MMP10 | +122% | 2.22 | |

"n.s" = not statistically significant;
linear changes >1.5-fold are listed in bold; linear changes <1.5-fold are listed in parentheses;
NQO1, TXNRD1, CASP14, and CTGF values have passed through a Benjamini-Hochberg false discovery rate (FDR) to adjust p-values (non-adjusted p-value and FDR p-values are both p ≤ 0.05).

The above Table 4 provides statistically significant (unpaired t-test, FDR p≤0.05, N=4) changes in gene expression for cashew testa extract versus the Vehicle Control group. As noted above, gene expression was analyzed in full-thickness in vitro skin culture tissue model. Additional analysis of the separate layers (epidermis and/or dermis) may identify additional changes in gene expression or enhance the fold-change values of those already regulated that may have been masked by analyzing both cell types together.

Metallothionein 1A ('MT1A') and Metallothionein 2A ('MT2A') are involved with antioxidant detoxification. Increased methalothionein leads to lower free radical activity, lower oxidative damage, and lower inflammation. Table 4 above indicates a significant increase in MT1A expression in the presence of cashew testa extract, indicating both antioxidant and anti-inflammatory activity in skin.

NAD(P)H:quinone oxidoreductase-1 ('NQO1') is an antioxidant, stress responsive gene that encodes for an enzyme that protects cells against chemical and radiation-induced oxidative damage. The AHR and NRF2 transcription factors control NQO1 expression. Levels of NQO1 are correlated with p63 expression in keratinocytes and dermal fibroblasts, and play a role in regulating cell proliferation and differentiation. NQO1 is associated with antioxidant detoxification, and can protect cells from further damage through slowing the degradation of tyrosinase. Table 4 above indicates cashew testa extract to significantly increase NQO1 expression and therefore function as an antioxidant.

Thioredoxin ('TXN') and thioredoxin reductase 1 ('TXNRD1') are involved in the antioxidant response of fibroblasts, as seen with exposure to $H_2O_2$, turning on the redox-sensitive signaling pathways to repair and defend against further insult. This allows for cellular adaptation to oxidative stress. TXNRD1 expression is downstream of NFE2L2 (nrf2) activation. TXNRD1 is also induced by exposure to resveratrol. Table 4 above indicates cashew testa extract to significantly increase TXNRD1 expression and therefore function as an antioxidant.

Caspase 14 ('CASP14') is a protease mainly expressed in the suprabasal layers of the epidermis. CASP14 is necessary for epidermal differentiation and cornification; CASP14 directly cleaves the filaggrin (FLG) protein monomer, most likely preparing it for breakdown by other proteases. Breakdown of FLG products by CASP14 leads to natural moisturizing effects in the skin.

Connective tissue growth factor ('CTFG') is a protein coding gene. Diseases associated with CTGF include Systemic Scleroderma and Renal Fibrosis. Among its related pathways are ERK Signaling and Gene Expression. Gene Ontology (GO) annotations related to this gene include growth factor activity and integrin binding. Overexpression of CTGF in fibroblasts promotes fibrosis in the dermis, kidney, and lung, and deletion of CTGF in fibroblasts and smooth muscle cells greatly reduces bleomycin-induced skin fibrosis. Table 4 indicates a significate reduction in the expression of CTFG in the presence of cashew testa extract, indicating that the extract may have activity in mitigating fibrosis, including possibly preventing significant increases in collagen thickening in dermal fibrosis.

Intercellular Adhesion Molecule 1 ('ICAM1') is a protein encoding gene that encodes a type of intercellular adhesion molecule continuously present in low concentrations in the membranes of leukocytes and endothelial cells. Upon cytokine stimulation, the concentrations increase greatly. ICAM-1 is an endothelial- and leukocyte-associated transmembrane protein long known for its importance in stabilizing cell-cell interactions and facilitating leukocyte endothelial transmigration.

Interleukin 1, alpha ('IL-1α') is an epidermal cytokine produced on a constitutive basis by keratinocytes. IL-1α acts as a "master regulator" of skin structure and function. IL-1α orchestrates dermal collagen turnover, and stimulates the production of hyaluronic acid. IL-1α can decrease melanogenesis through inhibition of tyrosinase activity. IL-1α production decreases with age contributing to compromised barrier function. IL-1α signaling triggers an inflammatory cascade important for tissue repair and wound healing.

Interleukin 1, beta ('IL-1β') is a cytokine upregulated during inflammatory response and is upregulated in barrier disruption. In skin disorders such as psoriasis, IL1β may disrupt epidermal homeostasis by blocking differentiation while proliferation persists. This cytokine is produced by activated macrophages as a proprotein, which is proteolytically processed to its active form by caspase 1 (CASP1/ICE). This cytokine is an important mediator of the inflammatory response, and is involved in a variety of cellular activities, including cell proliferation, differentiation, and apoptosis. Cashew testa extract significantly increased the expression of IL-1β, indicating a potential for its use in mediating skin inflammatory activity.

BIRC5 (survivin) is an anti-apoptotic protein that is expressed in a subpopulation of basal keratinocytes, most likely keratinocyte stem cells. BIRC5 has anti-apoptotic effects in cells exposed to UV; BIRC5 can inhibit apoptosis through inhibiting the activation of caspases. Overexpression of BIRC5 can rescue cells from p53-induced apoptosis. BIRC5 is upregulated in psoriasis, and overexpressed in aging dermal fibroblasts. Decreased expression of BIRC5, as shown in Table 4, suggests an anti-aging effect of cashew testa extract.

The above data demonstrates that the botanical extract of the testa of *Anacardium occidentale* L. has one or more compounds that exhibit inhibition of tyrosinase. Further, the in vitro studies of testa extract produced changes in genes related to antioxidant protection, cell renewal and regeneration, wound healing, anit-aging, and immune/inflammatory responses, suggesting that cashew testa extract increases the expression of antioxidant and anti-inflammatory related genes present in skin, while suppressing genes involved in excessive scarring of skin.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Further, unless defined otherwise, all technical and scientific terms used herein have the same meaning as commonly understood to one of ordinary skill in the art to which this invention belongs. Consequently, it is not intended that this invention be limited to the specific embodiments disclosed herein, but that it cover all modifications and alternatives coming within the true scope and spirit of the invention as embodied in the attached claims.

We claim:

1. A composition comprising:
   a botanical extract of the testa of the seed of *Anacardium occidentale* L.,
   wherein the botanical extract has been standardized to a catechin content of about 15.0 w/w % or greater, based on total weight of the extract, and
   wherein the botanical extract is present in the composition in a therapeutically effective amount of from about 125.0 µg/mL to about 1000.0 µg/mL,
   and a carrier,
   wherein the composition is effective in inhibiting tyrosinase activity.

2. The composition according to claim 1, wherein the composition is a cosmetic composition.

3. The composition according to claim 1, wherein the composition is a dietary supplement.

4. The composition according to claim 2, wherein the cosmetic composition is a skin whitening composition.

5. The composition according to claim 1, wherein the composition is a skin care composition.

6. The composition according to claim 3, wherein the dietary supplement is in solid dosage form and the carrier is chosen from gelatin, starch, magnesium stearate, talc, gums, silicon dioxide, stearic acid, cellulose and combinations thereof.

7. The composition according to claim 3, wherein the dietary supplement is in solid dosage form and the carrier is a functional carrier.

8. The composition according to claim 7, wherein the functional carrier is buckwheat or spelt.

* * * * *